US009506881B2

(12) United States Patent
Smits (10) Patent No.: US 9,506,881 B2
(45) Date of Patent: Nov. 29, 2016

(54) METHOD AND APPARATUS FOR PREDICTING A GROWTH RATE OF DEPOSITED CONTAMINANTS

(71) Applicant: MAPPER LITHOGRAPHY IP B.V., Delft (NL)

(72) Inventor: Marc Smits, Punacker (NL)

(73) Assignee: MAPPER LITHOGRAPHY IP B.V., Delft (NL)

( * ) Notice: Subject to any disclaimer, the term of this patent is extended or adjusted under 35 U.S.C. 154(b) by 506 days.

(21) Appl. No.: 14/345,656

(22) PCT Filed: Sep. 19, 2012

(86) PCT No.: PCT/EP2012/068444
§ 371 (c)(1),
(2) Date: Mar. 19, 2014

(87) PCT Pub. No.: WO2013/041569
PCT Pub. Date: Mar. 28, 2013

(65) Prior Publication Data
US 2015/0060701 A1    Mar. 5, 2015

Related U.S. Application Data

(60) Provisional application No. 61/536,295, filed on Sep. 19, 2011.

(51) Int. Cl.
*G01N 23/22*    (2006.01)
*G03F 7/20*    (2006.01)
(Continued)

(52) U.S. Cl.
CPC ............... *G01N 23/22* (2013.01); *B82Y 10/00* (2013.01); *B82Y 40/00* (2013.01);
(Continued)

(58) Field of Classification Search
USPC ................ 250/492.1, 492.2, 492.22, 492.23, 250/492.3
See application file for complete search history.

(56) References Cited

U.S. PATENT DOCUMENTS 6,545,274 B1    4/2003 Morita
7,494,753 B2    2/2009 Chen et al.
(Continued)

FOREIGN PATENT DOCUMENTS

JP         2010-010380        1/2010
WO    WO 2009 012919 A1    1/2009

OTHER PUBLICATIONS

S. Grantham, C., "The NIST EUV facility for advanced photoresist qualification using the witness-sample test", Extreme Ultraviolet (EUV) Lithography II, SPIE vol. 7969, 2011.
(Continued)

*Primary Examiner* — Nicole Ippolito
*Assistant Examiner* — Hanway Chang
(74) *Attorney, Agent, or Firm* — Hoyng Monegier LLP; David P. Owen (57) ABSTRACT

A lithography system (10) comprising a radiation projection system (20) for projecting radiation onto a substrate, a substrate transport system (30) for loading and positioning the substrate to be processed in the path of the projected radiation, a control system (40) for controlling the substrate transport system to move the substrate, and a resist characterization system (50) arranged for determining whether a specific type of resist is suitable to be exposed by radiation within the lithography system. The resist characterization system (50) may be arranged for exposing the resist on a surface of the substrate with one or more radiation beams, measuring a mass distribution of molecular fragments emitted from the resist, predicting a growth rate of deposited molecular fragments on the basis of a growth rate model and the measured mass distribution, and comparing the expected growth rate with a predetermined threshold growth rate.

16 Claims, 4 Drawing Sheets

(51) Int. Cl.
*H01J 37/304* (2006.01)
*H01J 37/317* (2006.01)
*B82Y 10/00* (2011.01)
*B82Y 40/00* (2011.01)
*G01N 33/00* (2006.01)

(52) U.S. Cl.
CPC ..... *G01N 33/0004* (2013.01); *G03F 7/70608* (2013.01); *G03F 7/70916* (2013.01); *H01J 37/304* (2013.01); *H01J 37/3174* (2013.01); *H01J 37/3177* (2013.01); *H01J 2237/022* (2013.01); *H01J 2237/31796* (2013.01)

(56) References Cited

U.S. PATENT DOCUMENTS

| | | |
|---|---|---|
| 7,955,767 B2 | 6/2011 | Dorsel et al. |
| 2002/0030801 A1 | 3/2002 | Endo et al. |
| 2006/0066824 A1 | 3/2006 | Knappe et al. |
| 2006/0108546 A1 | 5/2006 | Nagano |
| 2008/0304031 A1 | 12/2008 | Kanehira et al. |
| 2008/0315125 A1 | 12/2008 | Lorusso et al. |
| 2011/0102755 A1 | 5/2011 | Kawamura |

OTHER PUBLICATIONS

B.V. Yakshinskiy et al, "Carbon film growth on model electron-irradiated MLM cap layer: interaction of benzene and MMA vapor with TiO2 surface", Alternative Lithographic Techn.

K. Murakami, T. et al. "Contamination study on EUV exposure tools using SAGA Light Source (SAGA-LS)", Extreme Ultraviolet (EUV) Lithography, SPIE vol. 7636, 2010.

Hans Fosshaug et al. "Some aspects on mechanisms responsible for contamination of optical components in DUV lithographic exposure tools", Optical Microlithography XVIII, SPIE.

Julius Joseph Santillan et al, "A study of EUV resist outgassing characteristics using a novel outgas analysis system", Advances in Resist Materials, SPIE vol. 6519, 2007.

Gregory Denbeaux et al, "Quantitative Measurement of EUV Resist Outgassing", College of Nanoscale Science and Engineering University at Albany, SEMATECH, Austin, TX.

Rupert C. Perera, "Tooling to measure EUV resist outgassing anmd witness plate contamination",EUV Technology, Martinez, CA, 2010.

"Resist Outgas Testing", ASML.

Bas Wolschrijn et al, "New method for resist outgassing qualification", ASML.

Arnold Storm et al. "EUV-induced outgassing, Molecular contamination control for EUVL lithography tools", TNO Knowledge for business, TNO Science and Industry.

METHOD AND APPARATUS FOR PREDICTING A GROWTH RATE OF DEPOSITED CONTAMINANTS

BACKGROUND OF THE INVENTION

1. Field of the Invention

The invention relates to a growth of deposited contaminants in processing systems, and in particular to a method and an apparatus for predicting a growth rate of deposited contaminants resulting from deposition of gaseous contaminants outgassed from a substance undergoing processing by one or more radiation beams. The invention also relates to a lithography system comprising a resist characterization system and a method for determining suitability of a resist for use in a lithography system.

2. Description of the Related Art

The desire of the semiconductor industry to manufacture ever smaller device structures, for example for use in integrated circuits (ICs), drives the development of lithography systems using very low wavelengths. Examples of such systems include but are not limited to extreme ultraviolet (EUV) lithography systems and charged particle lithography systems which use electron or ion beams to provide a pattern onto a target substrate surface.

Components within lithography systems are susceptible to contaminants that are progressively deposited on their surfaces during operation of the lithography system. In particular, contaminants may be formed by reaction of molecular fragments that are stuck on surfaces of the system under the influence of radiation within the lithography system. For example, under irradiation with EUV or charged particle beams, gaseous hydrocarbons may form a layer of carbon on exposed surfaces of system components. The result of the deposition of the gaseous compounds on the surfaces of system components is that the reliability and/or operational accuracy of the lithography system decreases with time. Eventually, the lithography system is incapable of operating within preset requirements, and the malfunctioning components need to be cleaned or replaced. However, both cleaning and replacement of components is time-consuming and expensive, and results in a significant increase in downtime of the lithography system.

A significant source of gaseous hydrocarbons in lithography systems is the resist layer that is placed on top of a substrate surface to be exposed and is subsequently exposed to radiation, e.g. EUV or charged particles, such as electrons. A suitable resist may be selected to limit the contamination in a lithography system caused by molecular fragments ejected from a resist, in particular due to exposure of the resist to radiation beams. However, presently used methods for characterizing resists are labor intensive and time consuming.

BRIEF SUMMARY OF THE INVENTION

It is an object of the present invention to provide a method and an apparatus for characterizing a resist layer for use in a lithography system that can be easily applied in a limited period of time. For this purpose, the invention provides a lithography system comprising a radiation projection system for projecting radiation onto a substrate, a substrate transport system for loading and positioning the substrate to be processed in the path of the projected radiation, a control system for controlling the substrate transport system to move the substrate, and a resist characterization system arranged for determining whether a specific type of resist is suitable to be exposed by radiation within the lithography system. The resist characterization system may be arranged for exposing the resist on a surface of the substrate with one or more radiation beams, measuring a mass distribution of molecular fragments emitted from the resist, predicting a growth rate of deposited molecular fragments on the basis of a growth rate model and the measured mass distribution, and comparing the expected growth rate with a predetermined threshold growth rate. The resist characterization system is arranged for: exposing the resist on a surface of the substrate with one or more radiation beams; measuring a mass distribution of molecular fragments emitted from the resist; predicting a growth rate of deposited molecular fragments on the basis of a growth rate model and the measured mass distribution; and comparing the expected growth rate with a predetermined threshold growth rate.

Conventional methods for measuring the effect of deposited contaminants focused on measuring the potential or risk of contamination, rather than computing a growth rate based on the measurements. A computed growth rate can then be compared directly to a maximum growth rate permitted for a particular lithography system. A model to convert a measured outgassing rate to a growth rate of deposited contaminants can be used to enable such a computation of deposited contaminant growth rate.

Using conventional methods, the outgas spectrum of a resist can show a high outgas rate of low mass molecular fragments, and result in an indication as a "high risk" resist type. However, a computed growth rate of deposited contaminants for this outgas rate may be below the maximum growth rate threshold for a lithography system and the resist may be acceptable for use in the system.

Conventional methods measuring outgas rate and comparing to a threshold level of out gassing may be suitable for lithography systems using optical elements such as mirrors and glass lenses which may be affected by very low levels of deposited contaminants. In charged particle lithography and inspection systems, the lenses are formed by apertures through which charged particle beams pass, and deposited contaminants generally only become a problem when the apertures dimensions are significantly reduced by deposits forming in the apertures. The growth rate of the deposits is more significant in charged particle systems for properly determining the suitability of a resist for use in the system.

Further aspects of the invention are described in the appended claims and in the following description of embodiments of the invention.

BRIEF DESCRIPTION OF THE DRAWINGS

Various aspects of the invention will be further explained with reference to embodiments shown in the drawings wherein.

DESCRIPTION OF ILLUSTRATIVE EMBODIMENTS

The following is a description of various embodiments of the invention, given by way of example only and with reference to the figures. The figures are not drawn to scale and merely intended for illustrative purposes.

Certain embodiments of the invention will be described with reference to a charged particle lithography system, in particular an electron beam lithography system. As a result, deposition of carbon is assumed to result from the use of electron beams, and the formation of such carbon layer under the influence of an electron beam will be referred to as electron beam induced deposition (EBID). The skilled person will understand that such carbon layers may also develop under the influence of other types of radiation, such as ion beam radiation and EUV-radiation.

Throughout the specification reference is made to a "resist". This expression should be understood to relate to a material that is sensitive to radiation, such as the types of materials commonly used in lithography systems for patterning a substrate such as a silicon wafer. The resist may be a positive resist in which the portion of the resist that is exposed to the radiation becomes soluble in a further development process. Alternatively, the resist may be a negative resist in which the resist portion exposed to radiation becomes insoluble in a further development process. A resist is generally applied in the form of a thin layer on top of the substrate to be exposed to transfer the pattern that is exposed onto it to the substrate on which it resides.

Throughout the specification reference is made to "resist outgassing". This expression refers to radiation (e.g. EUV, charged particle, etc.) induced release of gaseous compounds and/or molecular fragments by a resist.

Figure 1:
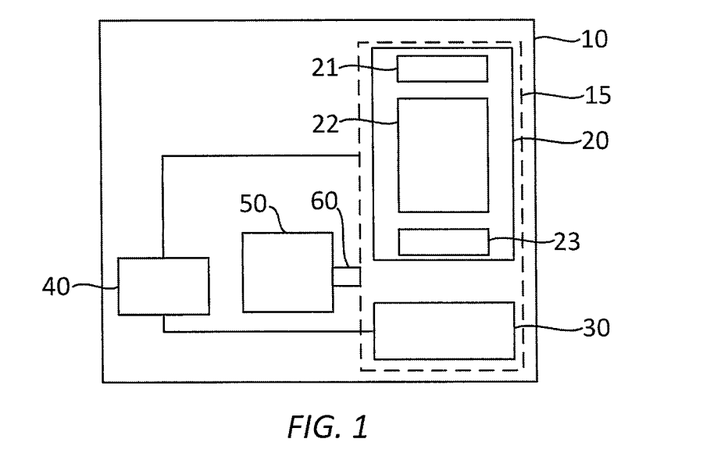
FIG. 1 shows a simplified schematic drawing of a lithography system according to an embodiment of the invention.

FIG. 1 shows a simplified schematic drawing of a lithography system 10 that may be used in embodiments of the invention. The lithography system 10 comprises a radiation projection system 20 for projecting radiation onto a substrate, such as a wafer, to be processed. The radiation projection system 20 may include a beamlet generator 21 for generating a plurality of beamlets, a beamlet modulator 22 for patterning the beamlets to form modulated beamlets, and a beamlet projector 23 for projecting the modulated beamlets onto a surface of a target. The components within the radiation projection system 20 are typically arranged in a column and are usually referred to as the electron-optical column or optical column, but may also be simply referred to as the "column". The radiation projection system 20 may be arranged to project any kind of suitable radiation, for example the system 20 may project of charged particle beams, optical beams, or other types of beams.

The lithography system 10 further comprises a substrate transport system 30 for loading a substrate and positioning the substrate to be processed in the path of the charged particle beams. The system 10 may then further comprise a control system 40 for controlling the substrate transport system 30 to move the substrate with respect to the radiation projection system 20. The control system 40 may base the movement on position information obtained by measurements within the radiation projection system 20, for example by the use of interferometry.

The lithography system further comprises a resist characterization system 50. The resist characterization system 50 is arranged for determining whether or not a specific type of resist can be exposed by radiation within the lithography system 10. The resist characterization system 50 may be coupled to the substrate transport system 30, for example via a load lock unit 60. The load lock unit 60 may then transfer a substrate, such as a wafer, provided with a resist layer to the lithographic apparatus for lithographic exposure.

Figure 2:
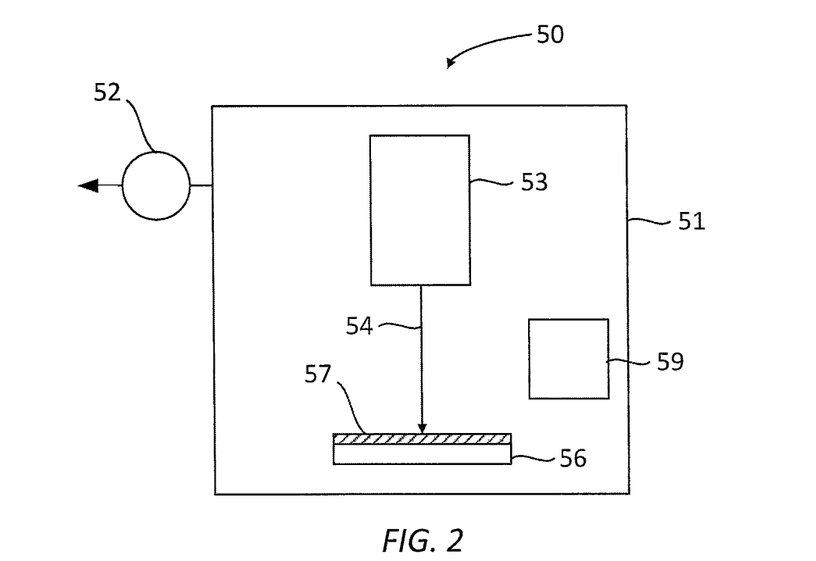
FIG. 2 schematically shows an embodiment of an apparatus for measuring a resist outgassing mass spectrum.

FIG. 2 schematically shows an embodiment of a resist characterization system 50. The resist characterization system 50 is arranged for measuring mass distribution of "outgassing" from the resist, i.e. gases emitted by the resist, particularly when exposed to a radiation beam. The apparatus 51 comprises a chamber 51 which may be pumped down to lower the pressure in the chamber using a pump system 52 known in the art. The apparatus 51 comprises a radiation source 53 for generating one or more radiation beams 54, a substrate 56 provided with a resist layer 57 on the surface, and a measurement device 59.

The resist layer 57 is exposed to the radiation beam(s) 54, and gaseous compounds originating from the resist layer 57 are measured with measurement device 59. The measurement device 59 may be a residual gas analyzer, for example a Microvision Residual Gas Analyzer of MKS Instruments. The measurement device 59 provides a resist outgas mass distribution. This results in a measured "fingerprint" of the resist layer 57 which may be used to predict the growth rate of outgassing contaminant deposition in the lithography system, as will be discussed in more detail with reference to FIG. 3.

Figure 3:
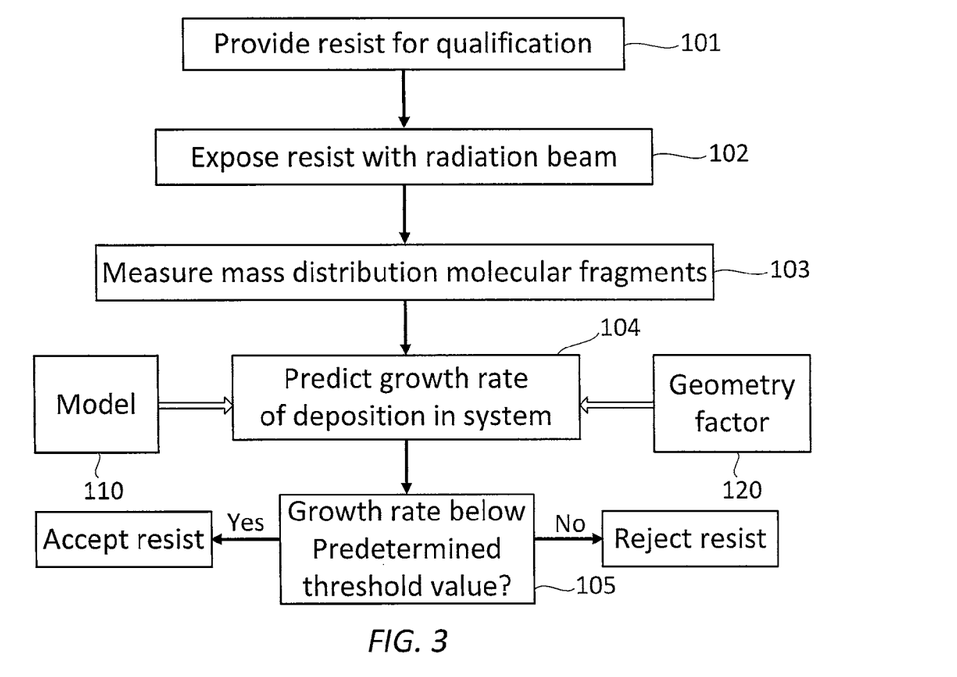
FIG. 3 shows a flow chart of a method of qualifying the suitability of a resist for use in a lithography system according to an embodiment of the invention.

FIG. 3 shows a flow chart of a method of qualifying the suitability of a resist for use in a lithography system according to an embodiment of the invention. The method will be described with reference to the resist characterization system 50 depicted in FIG. 2, although the method may be used in a different systems as well.

First, in action 101, the resist to be qualified is provided to the resist characterization system 50. The resist may be presented on a sample, for example a substrate such as a wafer. Alternatively, the resist may be put on a sample already present in the resist characterization system 50.

Then, in action 102, the resist is exposed by a radiation beam or beams. The radiation beam may comprises a plurality of beamlets. Preferably, the type of radiation used for the exposure corresponds to the type of radiation used in the lithography system in which the resist is to be used. Due to the radiation exposure, molecular fragments are released from the resist. The measurement device 59 measures the mass distribution of these molecular fragments in action 103.

The measurement results are then used to predict a growth rate of deposition in the lithography system in action 104. The prediction is based on the measurement results obtained in action 103. Additionally, a model 110 is used. The model is based on earlier measurements of radiation induced deposition caused by known molecular components, preferably using different radiation intensities. Further details with respect to the model 110 will be discussed with reference to FIGS. 4 and 5a-5c.

Preferably, the prediction of the growth rate is also based on a geometry factor 120 of the lithography system. The geometry factor is representative of the influence of the specific lithography system or type of lithography system on the growth rate of radiation induced deposition. The geometry factor may thus be different for different types of lithography systems. Further details with respect to obtaining a geometry factor of a lithography system will be discussed with reference to FIG. 6.

Finally, in action 105, the predicted growth rate of deposition in the lithography system is compared to a predetermined threshold growth rate value. Preferably, the predetermined threshold growth rate value corresponds to the maximum allowable growth rate in view of desired uptime requirements of the lithography system. If the predicted growth rate exceeds the predetermined threshold growth rate value, the resist is considered unsuitable for use in the lithography system, and thus rejected. If on the other hand, the predicted growth rate is below such predetermined threshold growth rate, the resist is considered suitable for use in the specific type of lithography system, and thus accepted.

This method of qualifying the suitability of a resist for use in a lithography system is relatively easy to perform and provides quick results without incurring high costs.

Embodiments of the method, or portions thereof, may be executed by a processor. The processor may be arranged to execute a computer program. Such computer program may be stored on a computer readable medium that can be loaded into a computer system comprising the processor.

The method for qualifying the suitability of a resist for use in a lithography system is not limited to predicting contaminant growth rate due to exposure to radiation beams, but can also be used applied without or before exposure, to measure outgassing of contaminants due to elevated temperature and other factors and the resulting contaminant growth.

The requirements for a resist may vary per type of lithography. For example, in EUV lithography, molecular fragments of elements and/or molecules that are difficult to remove by cleaning methods, such as molecules comprising and/or consisting of silicon, phosphor and sulphur, play a substantially equally important role as hydrocarbons. If a layer of only a few nanometers of non-cleanable residue is left on a mirror surface after cleaning, the quality of the optical properties of the mirror, in particular its reflectivity, is still reduce significantly. On the other hand, in the case of charged particle beam lithography, such as electron beam lithography, such "non-cleanable" molecules and/or elements play a less important role, since during the lifetime of an electron optical element, a much thicker layer of non-cleanable residue is acceptable. It has been found that transmission los starts to play a role for a layer of residue with a thickness greater than 100 nm.

Furthermore, the surface properties of optical components in an EUV lithography system are very different from the surface properties of optical components in a charged particle beam lithography system. Generally, some molecular fragments that are not cleanable in an EUV lithography system may actually be removable in a charged particle beam lithography system.

Figure 4:
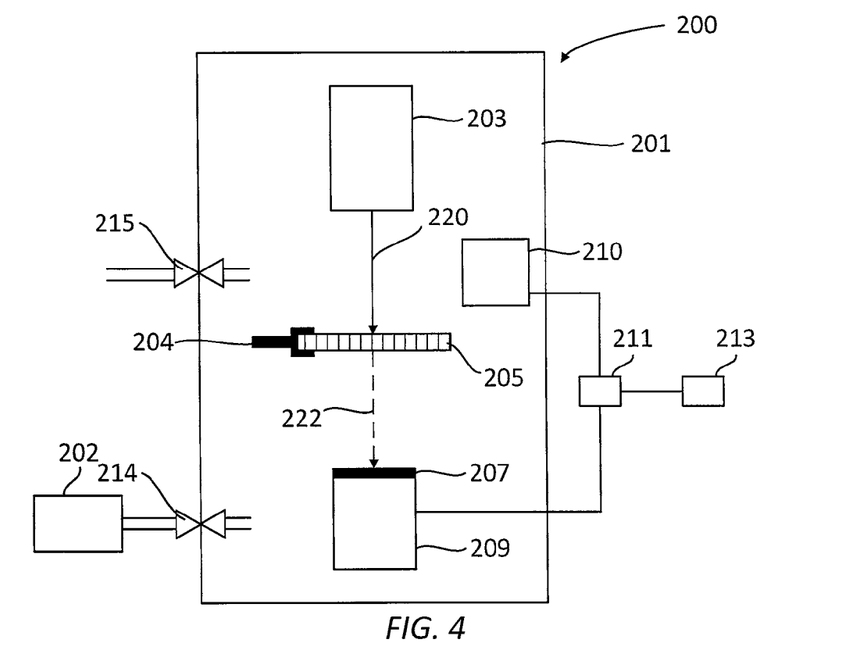
FIG. 4 schematically shows an embodiment of an apparatus that may be used for forming a growth radiation induced deposition growth rate model.

FIG. 4 schematically shows an embodiment of an apparatus 200 that may be used for forming a radiation-induced deposition growth rate model for use in the procedure of FIG. 3. The apparatus 200 comprises a chamber 201 suitable for containing a vacuum, and which can be pumped down using a pump system 202, preferably provided with a controllable opening, for example comprising a valve 214. The chamber includes a controllable inlet 215, for example by means of a suitable valve, for allowing predetermined gaseous compounds into the chamber 201. The apparatus 200 further includes a radiation source 203, a sample holder 204 for positioning a sample 205 in the path of the radiation beam(s), a radiation conversion element 207, a camera 209 and a measurement device 210.

In the shown embodiment, the radiation source 203 is an electron source arranged for generating an electron beam in the direction of the sample 205, in FIG. 3 schematically denoted by the arrow 220. The sample 205 may take the form of an aperture plate, i.e. a plate provided with a plurality of through holes, such as used in a charged particle lithography system. This may be an aperture array or beam stop plate such as used in a charged particle beam lithography system, or may be a plate specially constructed for the test apparatus. The presence of the aperture plate results in creation of a plurality of electron beamlets, the pattern of which corresponds to the pattern of the apertures in the plate. The plurality of electron beamlets is schematically denoted by the dashed arrow 222. The remainder of the electron beam is blocked by the sample plate.

The camera 209 is provided with a radiation conversion element 207 arranged for using energy obtained by the impact of electrons onto the conversion element 207 to create and emit photons. An example of such conversion element 207 would be a YAG (Yttrium-Aluminum-Garnet) scintillator. The plurality of electron beamlets formed by the aperture plate impinge on the conversion element 207 and form a plurality of light spots with a pattern corresponding to the pattern of electron beamlets. The light spots are then registered by the camera 209.

The use of an aperture plate allows the registration of radiation induced deposition in-line without the need to remove the sample 205 for further analysis. Consequently, the amount as well as the growth rate of the radiation induced deposition can be monitored over longer consecutive periods of time. Monitoring the radiation induced deposition parameters with the camera 209 allows for direct feedback. Furthermore, there is no need for characterization after the measurement, although such post characterization may be performed for checking purposes.

The controllable inlet 215 is arranged to enable a controlled entry of predetermined gaseous compounds, such as molecular fragments. The measurement device 210 is arranged for measuring the mass of contaminants being formed due to the interaction between the electron beam/beamlets and the predetermined gaseous compounds. The measurement device 210 may be a mass spectrometer, for example a Microvision Residual Gas Analyzer of MKS Instruments.

The measurement device 210 is communicatively connected to a processor 211. The processor 211 is also communicatively connected to the camera 209. The processor 211 may be further communicatively connected to a memory 213. The memory 213 and the processor 211 may be part of a single computer system, but they may also be located at different locations. The processor is arranged to perform calculations that enable the formation of a model. More details regarding this model formation will be explained with reference to FIGS. 5a-5c.

Figure 5A:
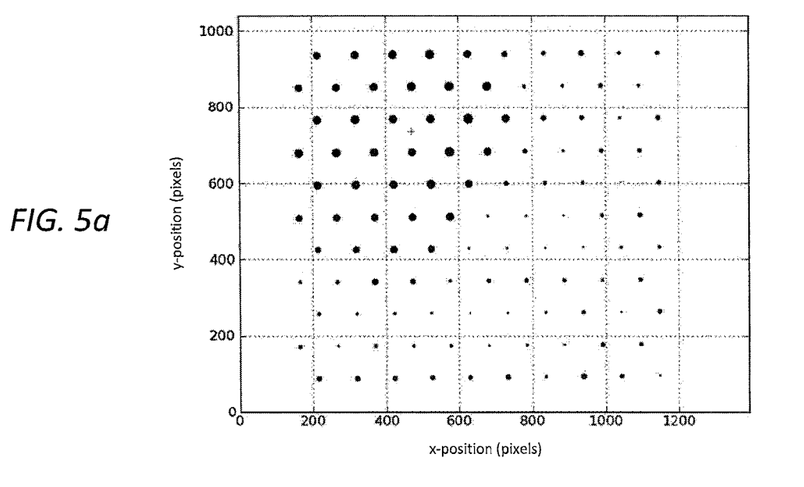
FIG. 5a shows an exemplary camera image made in the apparatus of FIG. 4.

FIG. 5a shows an exemplary camera image made in the apparatus of FIG. 4. The image shows a plurality of spots, which location corresponds to the location of the apertures in the aperture plate. The size of the spots varies as a result of radiation induced deposition clogging the apertures in the sample 205. The camera 209 is arranged to register the total transmission of (part of) the aperture plate 205. Due to the clogging of the apertures by contaminants (e.g. EBIDs), the transmission of beams through the sample aperture plate will decrease over time as the deposited contaminants build up and reduce the diameter of the apertures. By measuring the transmission loss of the aperture plate over time, the growth rate of the radiation induced deposition may be calculated.

Figure 5B:
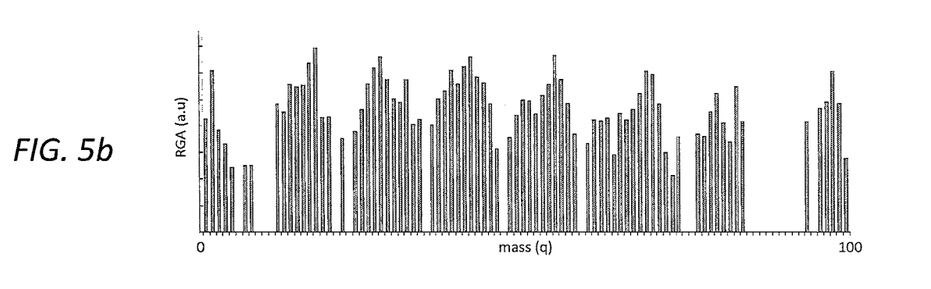
FIG. 5b shows an exemplary result of a mass spectrum measurement made within the apparatus of FIG. 4.
Figure 5C:
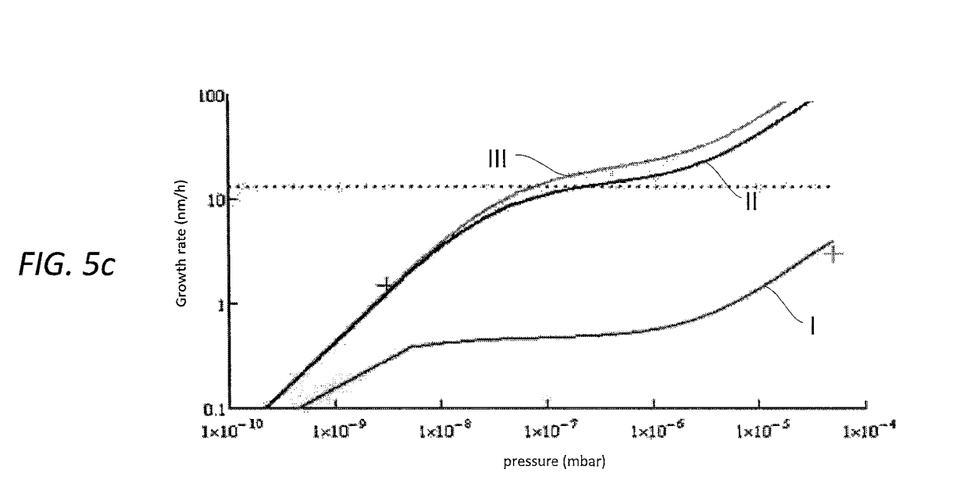
FIG. 5c schematically shows curves representing the growth rate as a function of contaminant partial pressure for different current densities.

FIG. 5b shows an exemplary result of a mass spectrum measurement with the measurement device 210, in this particular case a residual gas analyzer (RGA). In this example, the assumption is made that particles with a mass of 45 and higher play a role in radiation induced deposition. On the basis of the mass spectrum measured with the measurement device 210 a partial pressure can be derived by summation. The use of such summation is relatively easy and particularly suitable for use with lithography systems that are less sensitive to non-cleanable molecular fragments, such as charged particle lithography systems. FIG. 5c schematically shows curves representing the growth rate as a function of contaminant partial pressure for different current densities. In this specific example, curves I, II and III correspond to electron beam current densities 1 A/m$^2$, 30 A/m$^2$, and 45 A/m$^2$ respectively. The model is formed on the basis of growth rate curves, such as curves I, II and III. The forming of the model may be executed by a processor, such as processor 211 in FIG. 4. The processor may be arranged to execute a computer program. Such computer program may comprise elements that allow for performing a method of forming the model. The computer program may be stored on a computer readable medium that can be loaded into a computer system comprising the processor.

Figure 6:
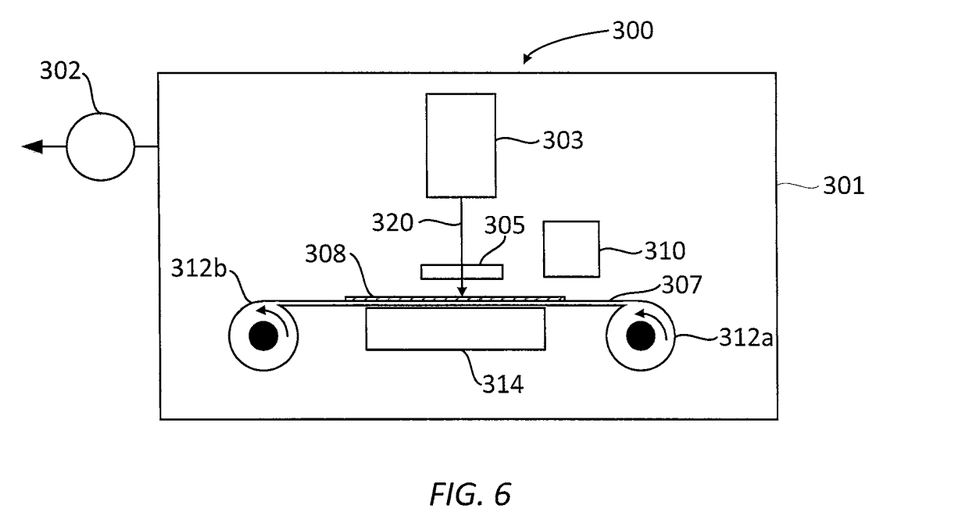
FIG. 6 schematically shows an embodiment of an apparatus for determining a lithography system geometry factor.

FIG. 6 schematically shows an embodiment of an apparatus 300 for determining a lithography system geometry factor. The apparatus 300 comprises a chamber 301 which can be pumped down using a pump system 302. The apparatus 300 comprises a radiation source 303 for generating one or more radiation beams 320, a sample holder for positioning a sample 305 in the path of the radiation beam(s), a tape 307 that can be moved in a direction substantially perpendicular to the radiation emitted by the radiation source and a measurement device 310.

The tape 307 is provided with a resist layer 308 (shown only on a portion of the tape, although it may be applied to an entire surface of the tape), preferably a resist of which mass spectrum measurements are taken to develop the model. The resist layer 308 is to be exposed in a way that mimics the exposure in a specific type of lithography system. For this reason, the tape 307 is continuously transported such that the radiation dose applied to the resist substantially corresponds to the dose such resist would receive in the type of lithography system under investigation. For transportation, the tape may be transferred, for example by means of two spools 312a, 312b as shown in FIG. 6. However, alternative methods for transferring the tape 307 are possible as well. To reduce thermal influences that will not take place within the lithographic system under investigation, the tape 307 may be suitably cooled by means of a cooling element 314.

Additionally, the sample 305 preferably corresponds to the most critical element in the lithography system under investigation, and its size and shape, as well as its position with respect to the resist, are preferably substantially identical to the size, shape and position of such element within the lithography apparatus under investigation.

In the shown example, the apparatus 300 is arranged for mimicking a multi-beamlet electron beam lithography apparatus. Therefore, the sample 305 takes the form of an aperture array. The actual exposure parameters may now be mimicked by choosing a suitable beam energy and a suitable transport speed of the tape 307 by rotating the spools 312a, 312b at a suitable rotation speed.

By mimicking the energy of the radiation impinging on the resist in combination with the geometry of the most vulnerable portion of the lithographic system under investigation, a reliable measurement of the resist outgassing may be obtained. The outgassing may be measured with the measurement device 310. After an exposure period that corresponds to a large number of wafer exposures in the lithography system under investigation, for example about 1000 or more, the sample 305 is removed from the apparatus 300 and the amount of radiation induced deposition is measured.

The apparatus 300 thus provides information on the influence of the geometry of the lithographic apparatus under investigation on the growth rate of radiation induced deposition, and is therefore referred to as the geometry factor. The geometry facture may improve the quality of the prediction of the radiation induced deposition growth rate in the lithography system. The geometry factor may be calculated using a processor communicatively coupled to the measurement device 310, for example the processor 211 depicted in FIG. 4.

The use of an apparatus 300 for determining a lithography system geometry factor is particularly useful for lithography system designs in which the final projection of the radiation onto the resist outgassing source, i.e. the substrate to be exposed, is executed by a lens system with a lens that is placed in very close proximity of the resist outgassing source. In terms of vacuum conductance, such projection system is extremely complex to model, and it is virtually impossible to obtain the actual pressure at locations within the projection system in a theoretical way. The apparatus 300 then enables determination of such pressures experimentally.

The invention has been described by reference to certain embodiments discussed above. It will be recognized that these embodiments are susceptible to various modifications and alternative forms well known to those of skill in the art without departing from the spirit and scope of the invention. Accordingly, although specific embodiments have been described, these are examples only and are not limiting upon the scope of the invention, which is defined in the accompanying claims.

The invention claimed is:

1. A lithography system comprising:
   a radiation projection system for projecting radiation onto a substrate;
   a substrate transport system for loading and positioning the substrate to be processed in the path of the projected radiation;
   a control system for controlling the substrate transport system to move the substrate; and
   a resist characterization system arranged for determining whether a specific type of resist is suitable to be exposed by radiation within the lithography system;
   wherein the resist characterization system is arranged for:
   exposing the resist on a surface of the substrate with one or more radiation beams;
   measuring a mass distribution of molecular fragments emitted from the resist;
   using a growth rate model, based on earlier measurements of radiation induced deposition caused by known molecular fragments for different partial pressures;
   predicting a growth rate of deposited molecular fragments on the basis of the growth rate model of molecular fragments and the measured mass distribution of molecular fragments, and deriving a partial pressure on the basis of the measured mass distribution of molecular fragments; and comparing the predicted growth rate with a predetermined threshold growth rate, the threshold growth rate being related to a maximum allowable growth rate in the lithography system.

2. The system of claim 1, wherein the radiation takes the form of one or more charged particle beamlets, and wherein the earlier measurements of radiation induced deposition are performed for different current densities of the one or more charged particle beamlets.

3. The system of claim 1, wherein the radiation projection system comprises a beamlet generator for generating a plurality of beamlets, a beamlet modulator for patterning the beamlets to form modulated beamlets, and a beamlet projector for projecting the modulated beamlets onto a surface of the substrate.

4. The system of claim 1, wherein the resist characterization system is coupled to the substrate transport system for transferring a substrate to the lithographic system for lithographic exposure.

5. The system of claim 1, wherein the resist characterization system comprises a chamber, a pump system arranged for pumping down the chamber to lower the pressure in the chamber; a radiation source for generating one or more radiation beams, a substrate provided with a resist layer on the surface, and a measurement device.

6. The system of claim 5, wherein the measurement device provides a resist outgas mass distribution.

7. The system of claim 5, wherein the measurement device comprises a residual gas analyzer.

8. A method for determining suitability of a resist for use in a lithography system, the method comprising:
    providing a substrate having the resist on a surface of the substrate;
    exposing the resist with one or more radiation beams;
    measuring a mass distribution of molecular fragments emitted from the resist;
    predicting a growth rate of deposited molecular fragments on the basis of a growth rate model of molecular fragments and the measured mass distribution of molecular fragments, the model being based on earlier measurements of radiation induced deposition caused by known molecular fragments for different partial pressures; and
    comparing the predicted growth rate with a predetermined threshold growth rate, the threshold growth rate being related to a maximum allowable growth rate in the lithography system.

9. The method of claim 8, wherein the radiation takes the form of one or more charged particle beamlets, and wherein the earlier measurements of radiation induced deposition are performed for different current densities of the one or more charged particle beamlets.

10. The method of claim 8, wherein predicting the growth rate of deposited molecular fragments is further based on a geometry factor, the geometry factor being representative of the influence of one or more properties of the lithography system.

11. The method of claim 10, wherein the geometry factor is representative of the influence of the geometry of the lithography system on the growth rate of the deposition.

12. The method of claim 8, wherein the model includes growth rates for a plurality of different molecular fragments.

13. The method of claim 8, wherein the model includes growth rates for different intensities of the radiation beam.

14. The method of claim 8, wherein deriving the partial pressure comprises summation using the measured mass distribution of the molecular fragments.

15. A method for predicting a growth rate of deposited contaminants resulting from deposition of gaseous contaminants outgassed from a substance undergoing processing by one or more radiation beams, the method comprising:
    exposing the substance with the one or more radiation beams;
    measuring a mass distribution of molecules and molecular fragments of the contaminants emitted from the substance;
    predicting a growth rate of deposited molecules and molecular fragments of the contaminants on the basis of a growth rate model and the measured mass distribution of molecular fragments, the model being based on earlier measurements of radiation induced deposition caused by known molecular fragments for different partial pressures; and
    comparing the predicted growth rate with a predetermined threshold growth rate, the threshold growth rate being related to a maximum allowable growth rate in the lithography system.

16. An apparatus for predicting a growth rate of deposited contaminants resulting from deposition of gaseous contaminants outgassed from a substance undergoing processing by one or more radiation beams, the apparatus comprising:
    a chamber;
    a pump system arranged for pumping down the chamber to lower the pressure in the chamber;
    a radiation source for generating the one or more radiation beams;
    a substrate provided with the substance on a surface of the substrate;
    a measurement device for measuring a mass distribution of the gaseous contaminants outgassed from a substance; and
    a processor configured to predict a growth rate of the deposited contaminants on the basis of a growth rate model of molecular fragments and the measured mass distribution of molecular fragments, the model being based on earlier measurements of radiation induced deposition caused by known molecular fragments for different partial pressures.

* * * * *